US009549998B2

(12) United States Patent
Kattumuri et al.

(10) Patent No.: US 9,549,998 B2
(45) Date of Patent: Jan. 24, 2017

(54) STABILIZED GOLD NANOPARTICLE AND CONTRAST AGENT

(75) Inventors: Vijaya Kattumuri, Surrey (CA); Kattesh V. Katti, Columbia, MO (US); Evan Boote, Columbia, MI (US); Raghuraman Kannan, Columbia, MO (US); Stan Casteel, Auxvasse, MO (US); Robert Churchill, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 941 days.

(21) Appl. No.: 12/665,086

(22) PCT Filed: Jun. 27, 2008

(86) PCT No.: PCT/US2008/008093
§ 371 (c)(1),
(2), (4) Date: Jun. 28, 2010

(87) PCT Pub. No.: WO2009/005752
PCT Pub. Date: Jan. 8, 2009

(65) Prior Publication Data
US 2010/0266508 A1 Oct. 21, 2010

Related U.S. Application Data

(60) Provisional application No. 60/937,475, filed on Jun. 28, 2007.

(51) Int. Cl.
*A61K 49/04* (2006.01)
*A61B 6/00* (2006.01)
*B82Y 5/00* (2011.01)

(52) U.S. Cl.
CPC ........... *A61K 49/0428* (2013.01); *A61B 6/508* (2013.01); *B82Y 5/00* (2013.01)

(58) Field of Classification Search
None
See application file for complete search history.

(56) References Cited

U.S. PATENT DOCUMENTS

| | | | |
|---|---|---|---|
| 3,717,701 A | 2/1973 | Carlson | |
| 5,948,386 A | 9/1999 | Katti et al. | |
| 6,818,199 B1 | 11/2004 | Hainfeld et al. | |
| 2003/0185757 A1* | 10/2003 | Kresse et al. | 424/9.32 |
| 2005/0054613 A1 | 3/2005 | Katti et al. | |
| 2006/0045916 A1 | 3/2006 | Raghuraman et al. | |
| 2006/0234248 A1 | 10/2006 | Sun et al. | |
| 2007/0051202 A1 | 3/2007 | Raghuraman et al. | |

FOREIGN PATENT DOCUMENTS

WO    WO 03/072053    9/2003

OTHER PUBLICATIONS

El-Sayed IH, Huang X, EL-Sayed MA. Surface plasmon resonance scattering and absorption of anti-EGFR antibody conjugated gold nanoparticles in cancer diagnostics: applications in oral cancer. 2005 Nano Lett. 5: 829-834.*
Kattumuri V. "Gold nanoparticles for biomedical applications: synthesis, characterization, in vitro and in vivo studies". Dec. 2006, PhD dissertation, University of Missouri—Columbia. Available online at https://mospace.umsystem.edu/xmlui/handle/10355/4398.*
Liu S, Zhang Z, Han MY. Nanometer-sized gold-loaded gelatin/silica nanocapsules. 2005 Adv. Mater. 17: 1862-1866.*
Nath N, Chilkoti A. A colorimetric gold nanoparticle sensor to interrogate biomolecular interactions in real time on a surface. 2002 Anal. Chem. 74: 504-509.*
Hainfeld JF, Slatkin DN, Smilowitz HM. The use of gold nanoparticles to enhance radiotherapy in mice. 2004 Phys. Med. Biol. 49: N309-N315.*
Huda W, Scalzetti EM, Levin G. Technique factors and image quality as functions of patient weight at abdominal CT. 2000 Radiology 217: 430-435.*
Varvarigou A, Bouziotis P, Zikos C, Scopinaro F, De Vincentis G. Gastrin-releasing peptide (GRP) analogues for cancer imaging. 2004 Cancer Biother. Radiopharm. 19: 219-229.*
Haidekker et al. Influence of gold nanoparticles on collagen fibril morphology quantified using transmission electron microscopy and image analysis. 2006 BMC Med. Imaging 6: 7 p. Published May 31, 2006.*
Balogh, Lajos P. et al., "Development of dendrimer-*gold radioactive nanocomposites to treat cancer microvasculature*," PharmaChem 2(4): 94-44, 2003
Bhattacharya, Santanu et al. "Synthesis of gold nanoparticles stabilised by metal-chelator and the controlled formation of close-packed aggregates by them," Proc. Indian Acad. Sci. (Chem. Sci), vol. 115, Nos. 5 & 6. pp. 613-619, (Oct.-Dec. 2003).
Connely, Neil G. et al. "Nomenclature of Inorganic Chemistry IUPAC Recommendations 2005," *International Union of Pure and Applied Chemistry*, 2005, p. 51-52.
Gardea-Torresdey, Jorge, "Plants with Midas Touch: Formation of Gold Nanoparticles by Alfalfa Plants," University of Texas at El Paso., Jul. 2002. Available online at: http://www-ssrl.slac.stanford.edu/research/highlights_archive/alfalfa.html.
Gierad, D. S, et. al., "Gadolinium as a CT contrast agent: Assessment in a porcine model" *Radiology* 1999, 210, 829-834.
HE, S. et. al.,"Superlattices of Silver Nanoparticles Passivated by Mercaptan,"*Journal of Physics D: Applied Physics* 34, 3425-3429 (2001).
Kalaugher, L., "Green Technique Makes Silver Nanoparticles," Nanotechweb.org., (Jan 2004).

(Continued)

*Primary Examiner* — Michael G Hartley
*Assistant Examiner* — Jennifer Lamberski
(74) *Attorney, Agent, or Firm* — Greer, Burns & Crain, Ltd.; Steven P. Fallon

(57) ABSTRACT

A kit for providing a contrast enhancer in a mammal for contrasting during imaging of the mammal comprises functionalized gold nanoparticles configured to be directed to one or more of a target organ, tissue and lesion of the mammal.

9 Claims, 5 Drawing Sheets

(56) References Cited

OTHER PUBLICATIONS

Kim, Beomseok et al., "Tuning the Optical Properties of Large Gold Nanoparticle Arrays," Mat. Res. Soc. Symp. Proc. vol. 676, Materials Research Society (2001).

Kim, Beomseok et al., "Self-Organization of Large Gold Nanoparticle Arrays," *J. Am. Chem. Soc.*, 123, 7955-7956 (2001).

MedCompare Contrast Agents. Accessed Aug. 30, 2011. Available online at: http://www.medcompare.com/matrix/165/Contrast-Agents.html.

Pastoriza-Santos, I. et al., "Reduction of Silver Nanoparticles in DMF. Formation of Monolayers and Stable Colloids," *Pure Appl. Chem.*, vol. 72, Nos. 1-2, pp. 83-90 (2000).

Prabhu, Kandikere Ramaiah et al. "De novo synthetic design for air-stable bis primary phosphines: Synthetic, catalytic and biomedical motifs," *Special Section: Non-Metal Chemistry; Current Science*, vol. 78, No. 4, Feb. 25, 2000.

Raghuraman, K. et al., "Characterization of Supramolecular $(H_2O)_{18}$ Water Morphology and Water-Methanol $(H_2O)_{15}(CH_3OH)_3$ Clusters in a Novel Prosperous Functionalized Trimeric Amino Acid Host," *J. Am. Chem. Soc.*, 125 (23) pp. 6955-6961 (2003).

Raveendran, P. et al., "Completely "Green" Synthesis and Stabilization of Metal Nanoparticles," *Journal of the American Chemical Society*, Oct. 22, 2003, 125(46), pp. 13940-13941.

Spring, D. B.; et. al., "Safety of ionic and nonionic contrast media Dr Spring and colleagues respond." *Radiology* 1998, 206, 560-561.

Spring, D. B.; et. al., "Nonfatal adverse reactions to iodinated contrast media: Spontaneous reporting to the US Food and Drug Administration, 1978-1994" *Radiology* 1997, 204, 325-332.

Spring, D. B.; et. al., "Deaths related to iodinated contrast media reported spontaneously to the US Food and Drug Administration, 1978-1994: Effect of the availability of low-osmolality contrast medial." *Radiology* 1997, 204, 333-337.

Volkert, W.A., T.J. Hoffman, "Therapeutic Radiopharmaceuticals," *Chem. Rev. (Review)* 99 (9); 2269-2292, 1999.

Yin et al., "Synthesis and Characterization of Stable Aqueous Dispersion of Silver Nanoparticles Through the Tollens Process," *J. Mater. Chem.*, 12, 522-527 (2002).

Rai, Mahendra et. al.,"CRC-675 Current Trends in Phytosynthesis of Metal Nanoparticles," *Critical Reviews in Biotechnology*, 2008, 227-284, vol. 28.

Kattumuri, Vijaya, et al.,"Gum Arabic as a Phytochemical Construct for the Stabilization of Gold Nanoparticles: In Vivo Pharmacokinetics and X-ray-Contrast-Imaging Studies," www.small-journal.com, 2007, 333-341, vol. 3: No. 2.

Markowitz, Michael A., et al,"The Effect of Membrane Charge on Gold Nanoparticle Synthesis via Sufactant Membranes," *Journal of Colloid and Interface Science*, 1999, 73-85, vol. 210.

Chanda, Nripen, et al,"Radioactive gold nanoparticles in cancer therapy: therapeutic efficacy studies of GA-[198] AuNP nanconstruct in prostate tumor-bearing mice," *Nanomedicine*, 2010, 201-209, vol. 6.

\* cited by examiner

Pig #147   No AuNP

Pig #150
47 mg Au (as AuNP)
per kg body weight
Δ HU ~ 12

STABILIZED GOLD NANOPARTICLE AND CONTRAST AGENT

PRIORITY CLAIM

Applicants claim priority benefits under 35 U.S.C. §119 on the basis of Patent Application No. 60/937,475, filed Jun. 27, 2008.

STATEMENT OF GOVERNMENT INTEREST

This invention was made with Government assistance under NIH Grant No CA 119412. The Government has certain rights in this invention.

FIELD

A field of the invention is nanotechnology. Example applications of the invention include X-ray computed tomography imaging.

BACKGROUND

X-ray Computed Tomography (CT) is the most widely used imaging modality for the diagnosis of various disease and disorders in animal and human population. Iodinated agents are routinely used as contrast enhancers to produce clinically intelligent images via X-ray CT. However, iodinated agents suffer from several drawbacks. One drawback is that the resolution of CT to detect cancer and other disorders within the body using iodinated agents at early stages of cancer development is limited by the inadequate contrast between the healthy and cancerous tissues. Another issue is that some patients develop allergic reactions as a result of administration of iodinated agents. Also, iodinated agents rapidly wash off clear from tissues, which impedes continuous monitoring of patients images through CT. Iodinated agents are also non specific, which prevents highly targeted imaging of specific tissue regions.

CT imaging uses special x-ray equipment to produce multiple images or pictures of the inside of the body and a computer to join them together in cross-sectional views of the area being studied. The images can then be examined on a computer monitor or printed. CT scans of internal organs, bone, soft tissue and blood vessels provide greater clarity than conventional x-ray exams. Because of its great sensitivity and specificity, CT scanning is often the preferred method for diagnosing many different cancers, including lung, liver and pancreatic cancer, since the image allows a physician to confirm the presence of a tumor and measure its size, precise location and the extent of the tumor's involvement with other nearby tissue. CT scans have also become pivotal medical diagnostic modality in examination that play a significant role in the detection, diagnosis and treatment of vascular diseases that can lead to stroke, kidney failure, and death.

Iodinated agents sometimes referred to as "dye", which are liquids, are used as CT contrast enhancers to produce images of specific organs, blood vessels and/or tissue types "stand out" with more image contrast to better show the presence of disease or injury. Thus, CT contrast highlights specific areas of the resultant CT image. While iodinated agents have become 'work horses' of medical CT imaging modality, they suffer from the major disadvantages discussed above. In addition, the application of iodinated contrast agents is restricted in certain patients because of the impact of these agents on the renal function. With iodinated agents, some imaging studies are limited by the injected dose and the rate of dose injection.

Certain types of diseases including, cancers should be monitored via imaging for a long period of time. For example, over 25% of patients with colorectal cancer develop metastasis in liver within 2-4 months post surgery. However, there are no tumor markers for continuous staging of the metastasis in liver in patients after they have been operated for removal of colorectal tumors. Currently available iodinated agents for CT imaging are unsuitable as the contrast agent is not retained in the liver for a sufficient length of time. For these and other reasons, there is a considerable need for new contrast agents.

SUMMARY

One aspect of the invention is directed to a contrast agent, comprising gold nanoparticles and gum arabic stabilizing means for stabilizing the particles to be retained in living tissue for an extended period of time. Other aspects of the invention are directed to methods for imaging mammals including steps of using gold nanoparticles is a contrast agent. Although some methods of the invention will be illustrated herein through use of phantom tissue, mice, and swine, it will be understood that many methods of the invention are useful with any mammal including humans.

Still other embodiments of the invention are directed to kits including gold nanoparticles useful for performing medical imaging, including useful for performing methods of the invention. For example, a kit for providing a contrast enhancer in a mammal for contrasting during imaging of the mammal comprises functionalized gold nanoparticles configured to be directed to a target portion of the mammal.

DETAILED DESCRIPTION

Figure 1:
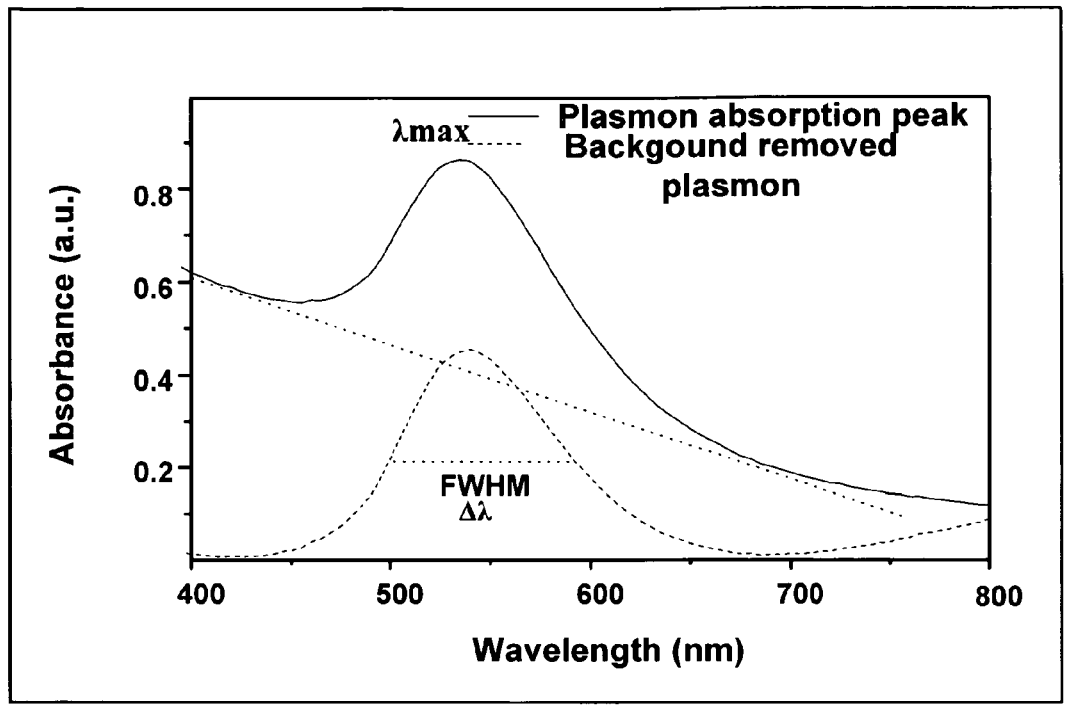
FIG. 1 illustrates absorbance characteristics of Au.

An embodiment of the invention is a stabilized and functionalized gold nanoparticle that is suitable for use as a contrast agent in CT imaging. Other embodiments include kits including particular concentrations and configurations of gold nanoparticles useful for performing medical imaging. Other embodiments include methods for performing imaging using such nanoparticles. Functionalized and stabilized gold nanoparticles (AuNP's) of the invention can enhance contrast in CT images attributed due to the high radio-opacity as compared to the tissue, and can remain in tissue for an extended period of time to permit repeat imaging. As illustrated by FIG. 1, Au exhibits useful absorbance characteristics. Stabilized and functionalized gold nanoparticles of the invention can serve as a powerful new contrast agent for clinical applications in the molecular imaging and therapy of various diseases and disorders in organs. Although some methods of the invention will be illustrated herein through use of Phantom tissue, mice, and swine, it will be understood that many methods of the invention are useful with any mammal including humans.

Before describing various example embodiments of the invention in detail, it will be appreciated that the invention includes gold nanoparticles useful for applications including medical imaging, kits including gold nanoparticles useful for performing medical imaging, and methods for performing imaging using gold nanoparticles. As used herein, the term "kit" is intended to broadly refer to an article, with an example being a supply of gold nanoparticles. It will be appreciated that in describing one embodiment of the invention, other embodiments may likewise be described. For example, a description of a method of the invention will be understood to likewise include description of kit of the invention useful to perform that method and a particle of the invention useful in practice of that method.

Nanoparticles of the invention, methods of the invention using and kits including stabilized nanoparticles provide a significant clinical benefit as they can be retained in tissue for significant time periods to permit repeated high contrast CT imaging. Methods of the invention, for example, may include steps of injecting a mammal with gold nanoparticles and then subjecting the mammal to imaging hours, a day, tens of days, or later. In some methods of the tension, the step of injecting the mammal is followed by repeated steps of imaging over periods of a few hours, 24 hours, several days, 10 days, 30 days, 60 days, 90 days, or longer. This offers important advantages and benefits over the prior art, since patients can be subjected to longer-term imaging without the requirement for repeated or frequent introduction of contrasting agent. The high levels of gold nanoparticles found in some organs long after injection also represents a surprising and unexpected result.

A method of the invention for performing imaging on a mammal, with an example being a human, using a contrast enhancer comprises the steps of introducing gold nanoparticles into the mammal and using an imaging apparatus to perform imaging on the mammal wherein the gold nanoparticles in the mammal enhance the contrast of images obtained. Likewise, a kit for performing such a method includes the gold nanoparticles prepared for introduction.

Some methods of the invention achieve particular benefits and utility through a further step of functionalizing the gold nanoparticles prior to the introduction into the mammal, while some kits include these functionalized nanoparticles. As used herein the term "functionalize" broadly refers to treating, conditioning, or otherwise operating on the gold nanoparticles to provide them with operative behavior or tendencies they did not previously have. By way of example, one example step of functionalizing a gold nanoparticle through a method of the invention includes combining the nanoparticle with a material or molecule having particular physical properties or characteristics the gold nanoparticles do not have. The nanoparticles may be functionalized to enhance their ability to engage a particular target organ, tissue, lesion or other desired portion of the mammal. In this manner, some methods and kits of the invention use a functionalized gold nanoparticle that is configured to engage only specific portions of interest of the mammal.

One particular example includes attaching a biomolecule to the gold nanoparticles. The biomolecule can be selected depending on the particular application at hand. For example, specific biomolecules can be chosen that are useful to engage one or more of blood clots, tumors, arterial plaque, particular organs, and particular tissues. As used herein, the term "engage" when used in this context will be understood to broadly refer to absorption, adsorption, adhesion or other physiological or mechanical connection or linkage between a molecule and an organ, tissue, lesion, blood clot, plaque, or the like. One example biomolecule useful in some methods of the invention is bombesin, which is known to be useful for engaging tumors such as prostate cancer tumors.

This illustrates one important advantage some invention embodiments. Gold nanoparticles have been discovered to be particularly suitable to functionalization. This is an advantage over many contrast agents of the prior art, with an example being iodine, that are much less suitable to being functionalized. This achieves benefits, including the ability to direct contrast agents specifically to targeted portions of the mammal, with an example being to a blood clot or an organs such as the kidney, spleen, liver, or the like. As a result, lower overall doses may be injected into the mammal since they can be directed to particular areas of interest.

It has also been discovered that there is some threshold of gold nanoparticle engagement with a target portion of the mammal that is useful to achieve a reasonable level of image contrast. This threshold varies with some factors, including background tissue, quantum noise statistics, the volume of the lesion, patient size, particular organ, and others. Nonetheless, a useful general threshold has been determined to be at least about 1 mg Au per gm of target. Some methods of the invention therefore include a step of causing engagement between target portion of the mammal in a ratio of at least about 1 mg gold nanoparticles per gram of target portion of the mammal. By way of example, if a 10 gm cancerous tumor were targeted, some methods of the invention include steps of engaging that tumor with at least 10 mg of gold nanoparticles and kits include providing this dosage of nanoparticle. Other methods of the invention may utilize engagement of other ratios of gold nanoparticles per unit mass of target portion of the mammal, with an example being less than 1 mg or 5 mg. As a general rule, a higher concentration is favored to produce the greatest level of contrast, although too high of concentrations may carry some health risks.

Still another advantage of some invention embodiments relates to the longevity of the gold nanoparticles as a contrast agent in a mammal following introduction. The utility of many prior art contrast agents was limited by relatively short operative presence of those agents following introduction to a patient. Taking radioisotopes as an example, they are known to have an operative lifespan of only 6 hours or so. Some methods of the invention, on the other hand, include steps performing imaging 24 hours, 10 days, 30 days, 90 days, or even more after the initial introduction.

This achieves important advantages and benefits over the prior art. For example, the patient can avoid repeated injections of a contrast agent that may have been required in the prior art for prolonged imaging. Through embodiments of the invention, a patient may receive an introduction of gold nanoparticles which will remain operative as a contrast agent for days, weeks, or even months. Imaging may be performed over these periods without the need for further introduction contrast agent.

Some embodiments of the invention, in fact, benefit through a delay between the initial introduction of the gold nanoparticles and the step of using an imaging apparatus to perform imaging on the patient. In some example methods, a step of waiting at least four hours after the introduction of gold nanoparticles is performed. It has been discovered that this time period is useful to allow functionalized gold nanoparticles to circulate and to engage targeted portions of the mammal. Other example methods of the invention include steps of waiting other periods, with examples being at least 1 hour, at least 24 hours, and at least 10 days. Different periods will result from different application conditions. Kits of the invention are configured to facilitate these delays.

Embodiments of the invention contemplate use of a variety of different imaging apparatuses to generate images of the mammal. One particular example that has proven to be useful is computed tomography, or CT. Other methods of the invention utilize other imaging apparatuses and techniques, with examples including linear tomography, poly tomography, zonography, or orhtopantomography, fluoroscopy, dual-energy computed tomography, CT scanners configured to perform energy discrimination, and others. Some methods of the invention have been discovered to be particularly well suited to practice with CT imaging.

For example, higher kVp values may be used with gold nanoparticle contrast agents than were practical (or in some cases possible) with some contrast agents of the prior art. "kVp" is a setting on an x-ray tube (whether a plain x-ray or CT scanner) that stands for "kilovolts peak". As the kVp setting is increased on an x-ray machine, the penetrability of the x-rays produced increases. When an x-ray machine emits x-ray photons, the energy of each photon is usually expressed in units of keV (kiloelectron volts). An electron volt ("eV") is the amount of energy required to move an electron through a one volt potential. A higher kVp setting results in photons with higher keVs because the greater acceleration of electrons in the x-ray tube results in more x-rays produced at higher energies. As the kVp setting is increased on an x-ray machine, the penetrability of the x-rays produced increases. X-rays produced in an x-ray tube have a spectrum of energies—the maximum photon energy will be no higher than the kVp. However, a higher kVp will produce a beam with a higher mean energy of x-ray photons in the spectrum. A higher photon energy means that the probability of penetration through a certain thickness of material increases.

Projection radiography typically uses kVp's around 70 to 85 kVp. This is dictated somewhat by the size of the patient and what type of body part is being examined. When iodine is used as a contrast agent, a maximum kVp is about 80. A typical CT scan uses a kVp of 120, although many scans today adjust this to 80 kVp (for pediatric CT to cut down radiation dose) and 140 kVp (necessary for the increasingly obese portion of the population).

For materials with higher atomic numbers, there is what is referred to as a "k-edge" in the x-ray attenuation. This occurs because the binding energy of electrons (the bond between these electrons and the nucleus of the atom) that increases with the atomic number of the element. One component of x-ray attenuation, photoelectric absorption (PE), does not occur unless the photon energy is greater than this binding energy. When the photon energy exceeds the k-shell binding energy, these two electrons are now available for PE. At this point, the attenuation of x-rays at that energy drastically increases—when plotted, it looks like an edge, hence the name "k-edge", referring to the k-shell electrons. Iodine has a k-edge energy of approximately 33 keV while gold's k-edge is about 80 keV.

Some embodiments of the invention include steps that exploit this. For example, some embodiments are suitable for performing CT imaging using a kVp of at least about 80, others of at least about 140. These levels are not available with some contrast agents of the prior art, including iodine. These levels are useful, however, to perform effective imaging in some applications including those in which patients have a large body thickness or mass. This is a particularly useful benefit given the increasing rate of obesity occurring in the U.S. and around the world which calls for higher kVp values than were previously practiced.

Still other example embodiments of the invention utilize selection of gold nanoparticle diameter for targeting specific organs, tissues, lesions, or other portions of the mammal. It has been surprisingly discovered that in some applications particle size is determinative on the likely end location of engagement of the nanoparticles within a mammal. For example, it has been discovered that nanoparticles having a diameter greater than about 20 nm are much more likely be finally engaged in the liver or the spleen, as opposed to nanoparticles having a diameter smaller than about 20 nm which are much more likely to be engaged in the lungs. This represents a surprising and unpredictable result, and some embodiments of the invention exploit this. Some methods of the invention, for example, include steps of selecting Au nanoparticle diameter based on target portion of the patient. Other embodiments include use nanoparticles with a diameter of greater than about 20 nm if the target portion of the mammal is the liver or spleen, and selecting nanoparticles having a diameter of less than about 20 nm if the target portion of the mammal is the lungs. Some kits of the invention include particles of these size ranges for use in imaging particular organs.

Embodiments of the invention also include a dosage of a set concentration of gold nanoparticles to introduce to the mammal. Higher dosage concentrations are generally favored over low for purposes of scan contrast agent. Too high of a concentration may be disfavored, however, for cost, potential health risk, and other reasons. It has been discovered that setting dosage concentration as a ratio to the body mass of the patient is useful to "normalize" over a patient population. Some embodiments of the invention, for example, include use of a dose having a concentration between about 2 and about 45 mg per kg body weight of the mammal, between about 2 and about 75 mg per kg, and some between about 1 and about 5 mg per kg body weight of the mammal. Other embodiments of the invention will utilize other concentrations. Embodiments of the invention include use a functionalized or targeted gold nanoparticle offer advantages in some applications of using significantly lower dose to the subject than would general (non-targeted) agents since the targeted particles can be directed to portions of the mammal of interest.

Some embodiments of the invention further include combining the gold nanoparticles with a stabilizing agent prior to introduction to the mammal. Stabilizing agents can be useful to improve handle ability of the gold nanoparticles, production of the gold nanoparticles, storage of gold and nanoparticles, or for other reasons. Some example stabilizing agents useful in embodiments of the invention include starch, agarose, glucose, and gum arabic. In some embodiments, the stabilizing agent may also have some functionalizing effect. Accordingly, a stabilizing agent may also be a functionalizing agent and visa versa. Gum arabic, for example, may have some stabilizing and functional properties.

Still other advantages of some invention embodiments relate to the tendency of gold nanoparticles under certain conditions to form nano arrays or to otherwise agglomerate and increase concentration in particular locations. Examples include particular organs, tumors, lesions, tissue, blood clots, plaques, and the like. Accordingly, some embodiments of the invention include steps of performing imaging only after nano arrays or other groupings of nanoparticles have formed in targeted portions of the mammal, or configuring nanoparticles to form such agglomerations.

Various embodiments of the invention are illustrated herein below using mammals including swine and mice. These experiments and experimental results not only illustrate various aspects of kits, nanoparticles, and methods of the invention, but they also illustrate benefits and advantages that are achieved through some example methods. Those knowledgeable in the art will appreciate that results with the mammal such as the swine or a mouse can translate to other mammals, including humans.

Experiments in pigs have demonstrated the efficacy of this stabilized particle for retention in liver for over 30 days for sustained CT imaging of liver and hepatic organs. The efficacy of this new CT imaging approach as demonstrated in large animals (in pigs) provides compelling evidence for utilization of gold nanoparticle based molecular imaging agents as biomarkers in imaging various organs in humans for the detection of various diseases and also for staging treatment response.

Some particular embodiments will now be discussed along with experimental results. Artisans will recognize broader aspects and additional features of the invention from the discussion of the example embodiments.

DEFINITIONS

| | |
|---|---|
| AuNP | Gold nanoparticle |
| AAS | Atomic Absorption Spectroscopy |
| AuNP-SS-BBN | Gold nanoparticle - bombesin conjugate |
| Bp | Bisphosphonate (Neridronate) |
| bp-GAAuNP | Gum arabic stabilized gold nanoparticles produced by bp |
| BSA | Bovine Serum Albumin |
| DI | De-ionized Water |
| GA | Gum Arabic |
| GAAuNP | Gum arabic stabilized gold nanoparticle |
| HEPES | N-2-Hydroxyethylpiperazine-N'-2-ethanesulfonic acid |
| HAS | Human serum albumin |
| IV | Intravenous |
| MES | 2-Morpholinoethanesulfonic acid |
| NAA | Neutron Activation Analysis |
| PBS | Phosphate Buffer concentrate (pH 7) |
| SAuNP | Starch stabilized gold nanoparticle |
| SS-BBN | Thioctic acid conjugated Bombesin |
| TEM | Transmission Electron Microscopy |
| THPAL | P[CH$_2$NHCH(CH$_3$)COOH]$_3$ |
| λmax | Plasmon wavelength |
| Δλ | Plasmon width |

EXPERIMENTAL

This section describes the synthesis of a library of functionalized gold nanoparticles for site specific localization of gold nanoparticles in liver, spleen, and lung; and will be useful to illustrate method steps of the invention. Methods of the invention include steps of using biomolecules that operate to enhanced adhesion, absorption, attachment or the like to specifically targeted organs or tumors. For example, tumor specific bombesin peptide functionalized gold nanoparticles allow localization of gold nanoparticles in prostate, small cell lung and breast cancer regions for subsequent tumor imaging using CT methods.

Synthesis of Gum Arabic Stabilized Gold Nanoparticles (GAAuNP) Contract Agents 0.012 g of gum arabic (GA) is dissolved in 6 mL of de-ionized (DI) water by heating the solution to 90-100° C. with continuous stirring. To this hot gum arabic solution, 0.1 mL of 0.1M NaAuCl$_4$ solution (0.0397 g in 1 mL DI) is added followed by the addition of 0.02 mL of 0.1M THPAL solution (0.0337 g in 1 mL DI) with continued stirring:

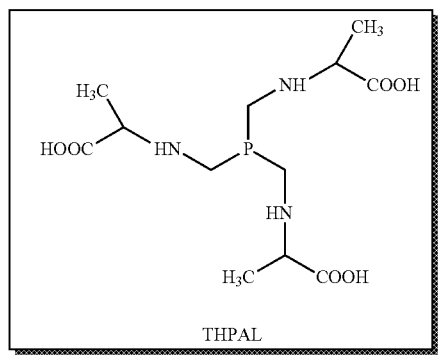

THPAL

When the color of the solution changes to reddish purple, stirring is continued for a minute without heating. The GAAuNPs thus formed are characterized by absorption and TEM measurements.

Possible Impurities: Traces of unreacted THPAL (<<10$^{-10}$ M), AuCl-4 (<<10$^{-10}$ M). These impurities can be eliminated by eluting nanoparticle solutions through Sephadex (G-100) as discussed in the purification section.

Synthesis of Gum Arabic Stabilized Gold Nanoparticles Produced by Bp-GAAuNP:

0.012 g of gum arabic (GA) is dissolved in 6 mL of de-ionized (DI) water by heating the solution to 90-100° C. with continuous stirring. To this hot gum arabic solution, 0.1 mL of 0.1M NaAuCl$_4$ solution (0.0397 g in 1 mL DI) is added followed by the addition of 0.4 mL of 0.1M bisphosphonate (bp) solution (0.0324 g in 1 mL DI) with continued stirring:

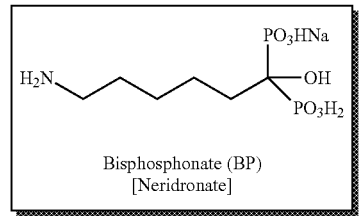

Bisphosphonate (BP)
[Neridronate]

When the color of the solution changes to reddish purple, stirring is continued for a minute without heating. The bp-GAAuNPs thus formed are characterized by absorption and TEM measurements.

Possible Impurities: Traces of unreacted by (<<10-10M), AuCl-4 (<<10-10M). These impurities can be eliminated by eluting nanoparticle solutions through Sephadex (G-100) as discussed in the purification section.

Purification Methods for GAAuNP and Bp-GAAuNP:

A Sephadex G-100 column was utilized to filter freshly prepared AuNPs. The different sized AuNPs diffused along the column at different rates under the effect of gravity. As the AuNPs start migrating along the column, coloration of Sephadex changes from white to purple. Pure AuNPs are eluted as purple colored fractions free of above mentioned impurities.

Synthesis of Gold Nanoparticle—Bombesin Conjugate (AuNP-SS-BBN Conjugate):

Synthesis of SAuNPs: 0.0225 g of starch is dissolved in 6 mL of de-ionized (DI) water by heating the solution to 90-100° C. with continuous stirring. To this hot starch solution, 0.1 mL of 0.1M $NaAuC_4$ solution (0.0397 g in 1 mL DI) is added, followed by the addition of 0.02 mL of 0.1M THPAL solution (0.0337 g in 1 mL DI) with continued stirring. When the color of the solution changes to pinkish purple, stirring is continued for a minute without heating. The gold nanoparticles (SAuNPs) thus formed are characterized by absorption and TEM measurements.

Purification: Sephadex G-100 column was utilized to filter freshly prepared SAuNP. The different sized AuNPs diffused along the column at different rates under the effect of gravity. As the AuNPs start migrating along the column, coloration of Sephadex changes from white to purple. Three fractions of SAuNPs are collected. Only the second fraction is utilized for SS-BBN conjugation. The second fraction is diluted by addition of DI water such that the plasmon peak absorbance is 0.7.

Bioconjugation: To 1 mL of filtered SAuNP solution, 1 mL of 0.885 µM SS-BBN (1 mg in 1 mL of methanol) solution was added and continuously stirred for 60-70 hours. At the end of stirring, the AuNP-SS-BBN sample precipitates out in the mixture and appears purple colored. The precipitate and supernatant are separated by centrifuging the mixture. The precipitate was further washed to extract purified AuNP-SS-BBN.

Purification: AuNP-SS-BBN precipitate was washed with DI water and vortexed for 2-3 min to re-suspend the particles. The solution was centrifuged at 13,000 rpm for 20 minutes in Fisher AccuSpin 400 micro-centrifuge to separate particles and supernatant. This procedure is followed two more times. Additionally, the precipitate was further washed with methanol three times. Re-suspension: The precipitate was dried in Savant Speed Vac concentrator for 20-25 min. The dry precipitate was weighed and re-dispersed in known amount of phosphate buffer concentrate of pH 7 by sonicating for 3-4 hours in Branson 2510 Sonicator. Only a part of precipitate dissolved in the buffer giving purple coloration to the solution. The supernatant was decanted and stored in a separate test tube. Water is added to the precipitate and sonicated for 0.5-2 hrs. The precipitate dissolves completely and is mixed with the supernatant removed earlier and sonicated for additional 1 hr. The final concentrations of the AuNP-SS-BBN conjugate solutions are in the order of ~0.5-1 mg/mL.

Transmission Electron Microscopy (TEM):

TEM was used to view and determine the size of AuNPs. TEM samples were prepared as follows: 5 µL of AuNP solution was placed on the carbon coated copper grid and allowed to sit for five minutes; excess solution was removed and the grid was allowed to dry for an additional five minutes to form a thin film of AuNPs. The average size and size distribution histogram of AuNPs were determined by digital processing of Transmission Electron Microscopy images using image processing software such as Adobe Photoshop (with Fovea plug-ins) or Image J.

IC50 Measurements:

Cancer Cell lines PC-3 were procured from the Cell Core Facility, University of Missouri—Columbia. The cancer cells are cultured in RPMI 1640 media and monitored through few passages (cell divisions) for the retention of original cell properties or else are discarded. The fresh good cells are placed in a media (1 g BSA and 2.46 g HEPS in 500 mL of RPMI1640) and are stored in refrigerator for later use (within 24 hrs). The pH of the media is set to 7.4 using NaOH and HCl before performing IC50 experiments. The cells are washed with the pH adjusted media twice. 50 µL of PC-3 cell solutions contain about 30,000 cancer cells respectively. Concentration of bombesin binding competitor, I-125-(Tyr4)-BBN(1-14)NH2 (iodinated-BBN), is adjusted such that 50 µL of iodinated-BBN corresponds to 20,000 counts in the γ-ray detector (Riastor Packard).

The AuNP-SS-BBN conjugate solutions are diluted in 1:3 serial dilutions to obtain at least 5-8 different concentrations. 50 µL of each of iodinated-BBN, AuNP-SS-BBN solution and cell solution are mixed in a centrifuge tube and vortexed. This mixture is then incubated for 40 minutes at ambient condition of 37° C., 5% $CO_2$ and 95% relative humidity. During the incubation, it is expected that most of the AuNP-SS-BBN is bound to the cells as it has better affinity towards the receptors on the cancer cells than that of iodinated BBN. After incubation, the mixture is placed in ice. 1 mL of ice-cooled media is added to 150 µL of the mixture, vortexed and centrifuged at 8000 rpm for a minute. The centrifugation separates the precipitate containing the iodinated-BBN and AuNP-SS-BBN bound cancer cells and supernatant containing unbound iodinated-BBN and AuNP-SS-BBN.

The supernatant is decanted and the precipitate is washed twice more with addition of 1.2 mL of cold media to remove unbound BBN. The tip of the centrifuge tube containing just the precipitate is cut and placed in a test tube and run through the γ-ray detector. The activity measured corresponds to the amount of iodinated-BBN left bound to the cancer cells upon addition of AuNP-SS-BBN. The activity of iodinated-BBN is measured for different concentrations of AuNP-SS-BBN. When almost all the iodinated-BBN is displaced by AuNP-SS-BBN, the activity measured is reduced by 95% of the original activity. IC50 value is the concentration of AuNP-SS-BBN that is responsible for reducing the activity of iodinated-BBN bound to cancer cells by half of the original activity. All chemicals were acquired from Fisher except RPMI 1640, acquired from GIBCO.

Details of Example In Vivo Embodiments

Swine Studies

Juvenile swine have been used to assess biodistribution patterns, clinical and clinicopathologic alterations, and pharmacokinetic behavior of AuNPs achieved through methods of the invention. The intravenous route of administration has been used in most of the in vivo assessments in the juvenile swine model after it was discovered that oral administration of AuNPs had <10% bioavailability. This low level of bioavailability represents an unexpected result. Steps of using oral administration, however, will be performed in some methods of the invention and will be useful for some particular applications.

One example method of the invention includes the biodistribution of a novel gold nanoparticle (AuNP) compound in gum arabic aqueous solution. This was assessed in juvenile swine by measuring with atomic absorption the concentration of gold in tissues. Three pigs were serially sacrificed at times ranging from 30 minutes to 24 hours after intravenous administration of 1.88 mg AuNP/kg of body weight. Heart, jejunum, brain, liver, spleen, kidney, and lung gold concentrations were determined to assess the tissue affinity for AuNPs in gum arabic. In a similar experiment, 5 groups of 3 pigs were given 1.88 mg/kg of THPAL-GAAuNP (pH 6-7) 0.322 mg/ml AuNP. Pigs were sacrificed at 30 minutes, 1 hour, 2 hours, 4 hours, or 24 hours according to group. Liver, kidney, spleen, small intestine, lung, heart and brain were collected for AA and NAA analysis. Average gold concentrations were lowest in brain and highest in the liver at all sampling times. At 24 hours post-dosing, the Au concentrations remaining in the liver and spleen were not significantly different from the 30 minute period suggesting a strong and sustained affinity of the AuNPs for these tissues. This is a surprising result and offers important advantages over the prior art. The AuNP do not decline in concentration over time as fast as markers of the prior art in these organs.

Three castrated male juvenile swine were acclimated for one week followed by the placement of central venous catheters. Pigs were dosed with Maltose-AuNP (0.3 mg Au/ml) IV at a dosage of 2.00 mg Au/kg body weight. Serial blood collection occurred at 5, 15, 30, and 60 minutes, then at 2, 4, 8, and 24 hours for gold analysis. Blood was also collected at time 0 minutes and 24 hours for serum biochemical profiles. Pigs were sacrificed following the final blood collection and lung, liver, kidney, spleen and brain tissues were collected for gold analysis. This preparation behaves very differently from the other AuNP preps in that levels in the liver were quite low with one pig liver below detection. None was detected in brain or kidney in any pig and the highest concentrations were found in the lung followed by the spleen.

Six intact male juvenile swine were assigned to one of two treatment groups. Pigs were dosed with bisphosphonate AuNP by either the IV or oral route, according to treatment group. Serial blood draw was performed at time 0, 5, 15, 30, and 60 minutes, then at 2, 4, and 24 hours for those pigs in group 1 (I.V.). Serum calcium was monitored at 0, 5, 15, 30, 60 minutes and 2 hours. Blood was collected at 1, 2, 4, and 24 hours for pigs in group 2 (oral). Four hour and 24 hour urine collections were analyzed for gold as a marker for excretion of the AuNP bisphosphonate for both groups. Pigs were sacrificed following the final blood collection and femur, liver and kidney tissues were analyzed by AA.

In a study to discern if gum arabic (GA) were interacting with a specific receptor, 3 pigs were given 20 mg/kg of 10 mg/ml filtered GA solution IV. 30 minutes following GA administration, pigs were given 1.88 mg/kg GA-AuNP 0.6 mg/ml solution and blood was collected at 5, 15, 30, 60, and 120 minutes. Blood was also drawn at 24 hours post-GA-AuNP administration just prior to sacrifice. Liver, kidney, spleen, and lung were collected for AA analysis.

In a second bisphosphonate experiment 20 castrated, male juvenile swine were assigned to one of 4 treatment groups. Pigs were dosed with bisphosphonate AuNP's in starch or Gum Arabic at either 2 or 4 mg/kg according to study design. Serial blood draw was performed at time 0, 5, 30, and 60 minutes, then at 2, 4, 24, 48, and 72 hours. Pigs were sacrificed following the final blood collection and femur, liver, lung and kidney tissues were collected for analysis. Heart, lung, liver and kidney tissue were collected into formalin for histopath.

In a 30-plus day study of GA-AuNPs, 2 pigs were given 0.3 mg/ml GA-AuNP solution at a dosage of 2 mg/kg IV. Pigs were bled for AA analysis of gold on days 7, 14, 21, 27 and 32. Certain serum samples were also selected for biochemical analysis to detect any untoward effects. Pigs were sacrificed following the final blood collection. Tissues collected included lung, liver, kidney, spleen, femur and brain will be collected for gold analysis and histopathologic examination.

GA AuNP multi CT scan: Pig 238 received multiple intravenous doses (as indicated below) of GA-AuNP. Tissues including lung, liver, kidney, spleen, and brain were collected for gold analysis and histopathologic examination.

| Dose | Date/time | Concentration | ML's given |
|---|---|---|---|
| 1 | Day 1 - 5 pm | 1.36 mg Au/ml | 120 |
| 2 | Day 2 - 8 am | 1.36 mg Au/ml | 160 |
| 3 | Day 3 - 5 pm | 1.36 mg Au/ml | 160 |

*pig 238 was found dead on Day 3 in the AM, and was necropsied at that time.

Mouse Studies
BBN-Mouse 2 mice were given either 1 ml or 0.5 ml Au-VK-39-SSBBN-C both died. 2 mice were dosed with 0.25 or 0.125 mls of the same solutions and survived although some depression was noted. A fifth mouse was given 0.5 mls of a starch AuNP solution and did fine. All surviving mice were euthanized at 2 hours post dosing and blood, pancreas, liver, kidney, spleen, and lung were collected, weighed and frozen for NAA analysis.

Tramp Study 1
Part A

Tramp mice (3 PBTag+ and 2 PBTag−) were give 0.1 ml SAuNP (0.7 mg/ml) IP. 2 Tramp mice both PBTag+ were given a starch solution, one received 1 ml and the other 0.73 ml. All mice were sacrificed at ~24-hours post-dosing and liver, kidney, spleen, pancreas and blood were collected and weighed for NAA. Prostate was also collected for archiving. Tail snips from each mouse were taken for genotyping.

Part B

2 PBTag+Tramp mice were dosed with 0.1 ml of 2.1 mg/ml Au-BBN solution IP. Both mice were sacrificed ~24 hours post-dosing and tissues were collected and weighed as above for NAA. Tail snips were also taken. Mouse 5184 has a prostate mass at necropsy.

Gold Nanoparticle Based Contrast Enhancement in Computed Tomography Using Tissue Mimics Contrast enhancement studies were carried out using phantoms as tissue mimics prepared from gum Arabic gold nanoparticle (GA-AuNP) constructs. Phantom images were obtained at 80 KVp and 140 KVp. A higher mean density of Au compared to the background results in a contrast differential ($\Delta HU$). Results from each concentration of GA-AuNP used in the computer tomography study and on the effect of cysteine are summarized herein below.

Variation in the pixel values may occur, both within the GA-AuNP sample regions and the background region. These would be reduced in size for thicker slices or for higher doses. At the lowest concentrations, the apparent contrast is negative. This is likely due to the fact that the background material is a tissue-mimic and therefore has a slightly higher density and effective atomic number than the aqueous GA-AuNP sample. There is a linear relationship between GA-AuNP concentration and $\Delta HU$. The slopes of both lines (80 kVp and 140 kVp) are approximately 25 HU per milligram of gold concentration per gram of background.

Computed tomography contrast is primarily due to electron concentration which, in approximation, is proportional to the physical density of individual voxels. It is believed that the high atomic number and greater absorption at 100 keV makes gold an ideal candidate for imaging contrast.

An advantage of methods of the invention utilizing gold nanoparticles is that the ability to circulate in the bloodstream reduces problems with timing of the CT scan following injection of the contrast agent. Furthermore, in some methods of the invention bioconjugation of nanoparticles will result in a certain uptake within volumes of interest (e.g. Lesions) and will cause a localized enhancement that will become apparent to the observer. Iodinated contrast agents are injected at high concentrations (300 mg/mL or 2.5 M) to achieve a contrast enhancement with a blood concentration of approximately 1 mg/mL (7.9 mM). Methods of the invention using targeted nanoparticle concentrations can achieve sufficient local concentration through an accumulation and build-up over time.

The uptake and concentration of contrast agent required to visualize lesions will be dependent upon a number of additional variables such as image noise, lesion size and lesion shape. All of these affect the receiver-operator characteristics of the imaging system in question. When presented with smaller "lesions" of 3 mm, an observer is able to detect these with a "critical contrast" of $\Delta HU=6$. This would represent a concentration of gold nanoparticles (against the background) of approximately 300 μg per ml or 1.5 mM. These results provide a basis for knowing the required uptake of AuNP in various organ systems or targeted lesions in order to provide sufficient contrast to differentiate against background structures.

Experiments were conducted for CT imaging of liver, vena cava and spleen in pigs using methods of the invention. These methods include steps of injection of specific concentrations of Gum Arabic/starch coated gold nanoparticles intravenously in pigs followed by CT imaging using a clinical CT scanner. Other stabilizing agents will be useful in other method embodiments, with examples including (but not limited to) agarose and glucose. The specific details of dose ranges and the CT imaging conditions are outlined in the following sections.

Example Method of the Invention: Gold Nanoparticle Based Contrast Enhancement in Computed Tomography in Mammals:

Gum Arabic stabilized gold nanoparticles were utilized in this example method of the invention. To evaluate the efficacy of contrast enhancement, juvenile swine were dosed with nanoparticles at a rate of approximately 2-45 mg of gold per kg body weight. Steps of introducing other concentration ranges are performed in other method embodiments. CT scans were acquired at several time intervals within two days of the injection using a standard, clinical CT scanner. Scans were obtained prior to dosing for evaluating the change in CT number due to the accumulation of gold in particular tissues. Scans were acquired at both 80 kVp and 140 kVp settings. Standard reconstruction methods and reconstruction filters were used and images were evaluated for the same slice location and for regions of interest over the entire organ in question. Animals were sacrificed following CT scans and tissues were analyzed for gold concentration using atomic absorption spectroscopy.

Within one day of gold nanoparticle administration, the average liver CT numbers increased by approximately 12 Hounsfield units (HU). This corresponded with an uptake of approximately 1.2 mg of gold per $cm^3$. There was a change of density within the spleen as well. Increased conspicuity of the hepatic vessels was perceived and endured (in additional scans) through the study. The observed increase in pixel HU showed that approximately 75% of the injected dose will be taken up in the liver.

This represents a useful discovery. In particular it suggests that the concentration and/or total amount of AuNP introduced may vary depending on the organ, tissue or tumor site of interest area because in some applications a majority of the AuNP are "stopped" at the liver, less is available for depositing in other organs. Accordingly, methods of the invention includes steps of determining the concentration and/or total amount of Au to be introduced to a mammal depending on which organ, tissue or tumor site is of interest.

Figure 3:
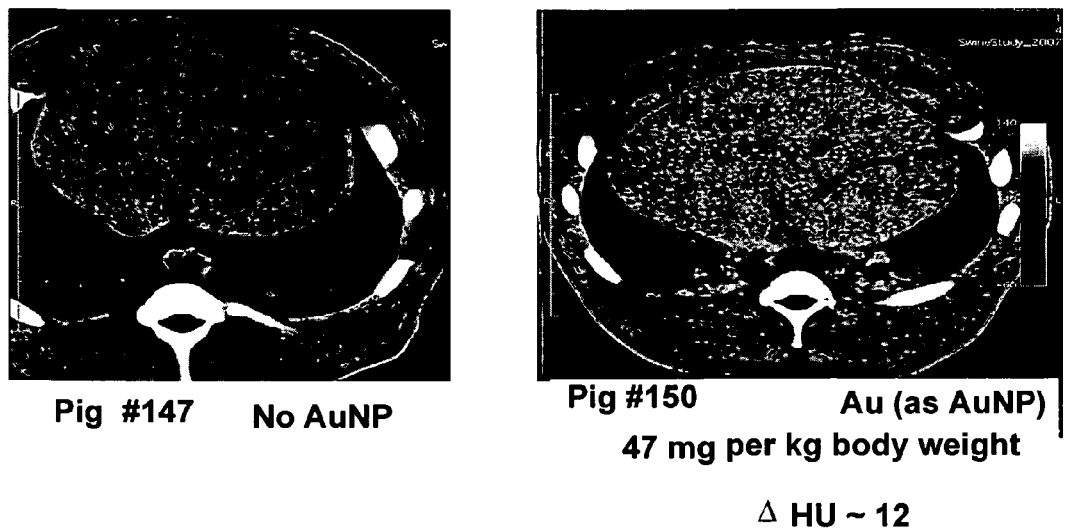
FIG. 3 illustrates CT scans of the same two swine livers at a different kVp level.
Figure 4:
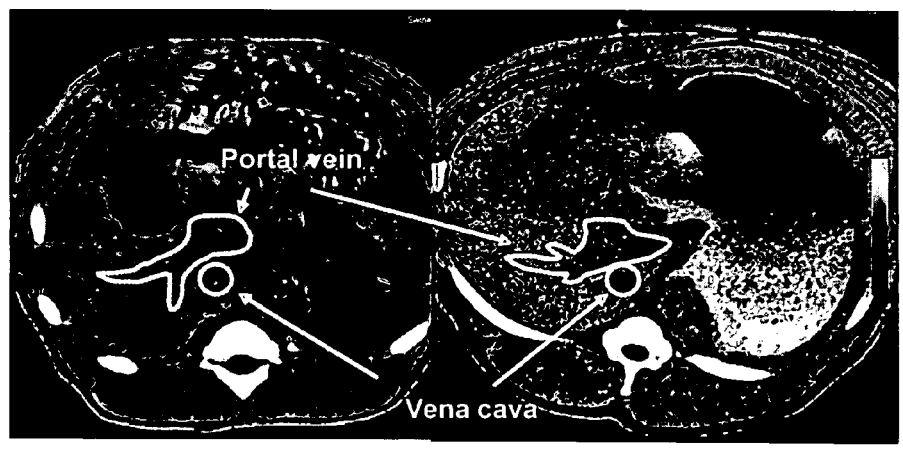
FIG. 4 illustrates an enhancement of CTE images taken after GA-AuNP injection.

The swine exhibited no change in clinico-path parameters. Long-term biodistribution studies indicate that nanoparticles of this formulation reside in the liver up to 30 days or more following administration. In some methods of the invention, Gum Arabic stabilized gold nanoparticles are used to enhance contrast in an animal model liver over an extended time. Importantly, the nanoparticles had no deleterious effect on the subject. CT Images of pig liver as obtained through gold nanoparticle contrast enhancements are shown in FIGS. 2-4.

Figure 2:
FIG. 2 illustrates CT scans of two swine liver samples.

FIG. 2 illustrates CT scans of two swine liver samples performed at 80 kVp, one with 47 mg/kg of bodyweight AuNP injected and one without any AuNP. FIG. 3 illustrates CT scans of the same two swine livers taken at 140 kVp. FIG. 4 illustrates an enhancement of CTE images taken after GA-AuNP injection. These Figures illustrate the contrast enhancements that are available through use of methods of the invention.

X-Ray CT In Therapy:

In methods of the invention, retention of high concentration of gold nanoparticles within mammal liver allows selective irradiation of liver using high energy X rays. These methods are valuable, among other applications, when treating primary and metastatic liver tumors. Irradiation with high energy X rays would lead to selective absorption of X rays only within the gold nanoparticles. The proximity of gold nanoparticles in specific organs (liver as shown in the current examples) ensure selective irradiation of tumor sparing the healthy tissue and thus, maximize the therapeutic pay load at the tumor. This approach is applicable for treating human patients with breast, prostatic and brain tumors as well.

Figure 5:
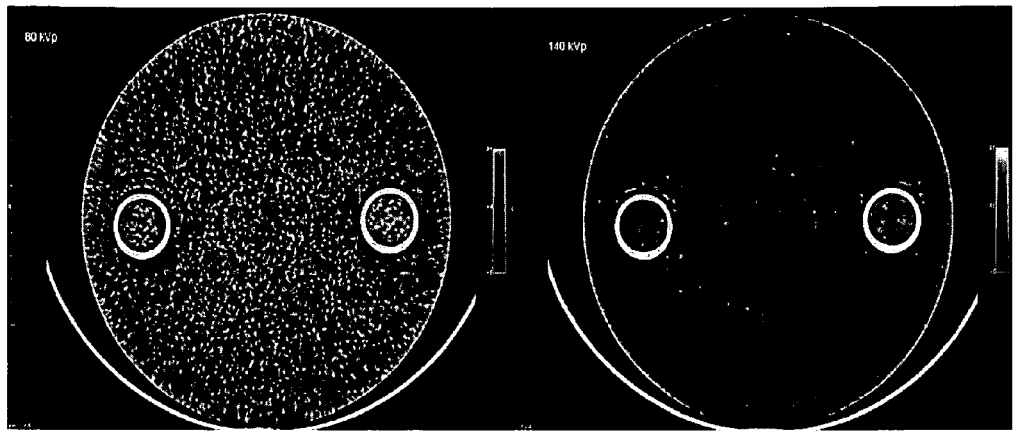
FIG. 5 illustrates scans of phantoms.

Contrast Enhancement Via GA-AuNP Vectors for Computed Tomography:

A Gammex/RMI Model 461 phantom was scanned using a Siemens Volume Zoom computed tomography system. Two 24 mL glass vials were filled with aqueous solutions of varying concentrations of GA-AuNP and were placed in holders in the phantom. This arrangement presented a tissue-like (solid water) background with GA-AuNP contrast inclusions. Scans were performed at tube voltages of 80 kVp and 140 kVp at the same level in the phantom. Images were reconstructed in 4 mm thick slices with a field of view of 208 mm. Results are illustrated in FIG. 5. This Figure shows computed tomography images of the phantom at 80 kVp (left) and 140 kVp (right). The vials containing GA-AuNP are at the 9 o'clock and 3 o'clock positions. A sample with 1.49 mg AuNP per gram background is in the 3 o'clock position and the 9 o'clock position has a sample with 0.9 mg AuNP per gram background.

Evaluation of the contrast enhancement contribution of GA-AuNP was done by loading the digital computed tomography images in a standard display program and then selecting a region of interest on the resultant computed tomography image for each sample and the background. Contrast enhancement is determined in $\Delta HU$ (HU=Hounsfield units) for each mass concentration of GA-AuNP and each tube voltage.

In Vitro Stability of Gold Nanoparticles:
Methodology-In vitro Stability:

The stability of AuNPs was evaluated by monitoring $\lambda$max and $\Delta\lambda$ over a reasonable period of time. The plasmon wavelength, $\lambda$max, corresponds to the mean size of the nanoparticles and plasmon width, $\Delta\lambda$, corresponds to the size distribution of nanoparticles. It should be noted that a shift in $\lambda$max is associated with either an increase in the mean size of the particles or modification in the surrounding media. Correspondingly, any change in $\Delta\lambda$ indicates either agglomeration of nanoparticles or modification in the surrounding media. A change of less than 10 nm $\lambda$max and $\Delta\lambda$ during certain time period was deemed adequate to consider AuNPs stable over that period of time in a particular media.

Figure 6:
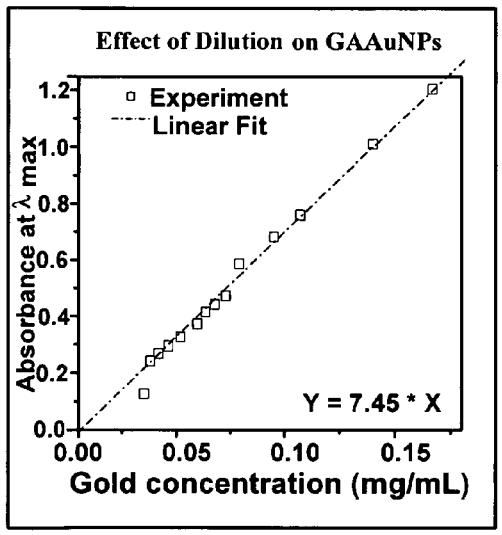
FIG. 6 illustrates the effects of Au dilution on absorbance.

The effect of dilution was evaluated by successive addition of 0.2 mL of DI water to 1 mL of gold nanoparticle solution and subsequent absorption measurements. FIG. 6 illustrates the results. There is a linear dependence of absorbance at $\lambda$max on the concentration of gold in accordance with Beer-Lambert's Law. It was found that both $\lambda$max and $\Delta\lambda$ are unaltered for GAAuNP concentration ranging from 0.24-2.4 nM.

Figure 7:
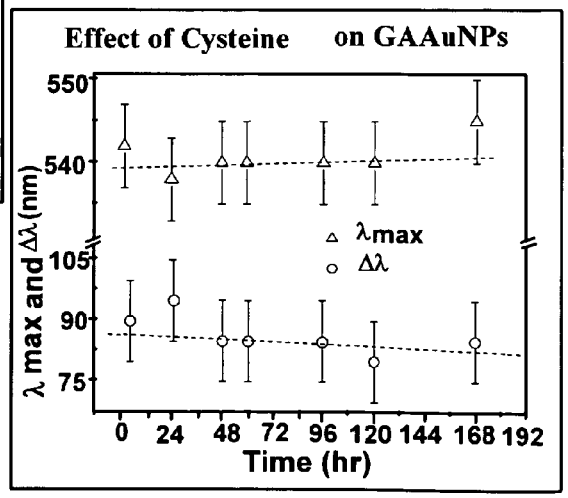
FIG. 7 illustrates the effects of cysteine on absorbance.

The stability of gold nanoparticles was also tested in presence of NaCl, cysteine, histidine and BSA solutions. 0.5 mL of 35% NaCl, 1% cysteine, 0.2M histidine and 2% BSA was added to 1 mL of gold nanoparticles solution and incubated for 30 minutes before taking the absorption measurements at different time points. FIG. 7 illustrates some results. An alteration of $\lambda$max and $\Delta\lambda$ of GAAuNPs occurs in cysteine over time. Following the benchmark of change of less than 10 nm in $\lambda$max and $\Delta\lambda$ during the observation time, GAAuNPs can be considered to be stable in the presence of cysteine over a 4 day period.

pH Stability: GAAuNP and bp-GAAuNP are stable at 3-8 pH, AuNP-SS-BBN stable at physiological pH.

Lyophilization and freeze thaw stability, filtration, dialysis, centrifugation: AuNP-SS-BBN is stable against lyophilization and freeze thaw stability, filtration, dialysis, centrifugation. These offer important advantages for stability when using methods of the invention.

In Vivo Stability Studies of Gold Nanoparticles:

Methods of the invention include steps of maintaining AuNP in vivo in mammals for extended time periods. Stability and pharmacokinetics properties of gold nanoparticles in aqueous solution were assessed in juvenile swine by measuring the percentage of gold content in various organs using Atomic Absorption Spectrometry (AAS) and Neutron Activation Analysis (NAA).

Clinical Route: Many methods of the invention utilize an intravenous route of administration. This was used in most of the in vivo assessments in the juvenile swine model after a brief pilot study indicated that oral administration of AuNPs had <10% bioavailability. The benefits including a much higher bioavailability achieved through intravenous introduction represent a surprising result. Some kits of the invention include an apparatus for introducing the nanoparticles intravenously, with examples including a catheter, a syringe, and the like. In some methods of the invention and for some particular applications however, oral administration will be a useful step.

Bio-Distribution Studies with GAAuNP and bp-GAAuNP

Male juvenile pigs weighing 10-15 kg were acclimatized for a week, at the end of which catheters were placed in their jugular vein for intravenous administration of AuNP solutions and blood draws. Freshly synthesized gold nanoparticles solutions (GAAuNP and bp-GAAuNP) were pH adjusted to physiological pH by adding appropriate amount of phosphate buffer (pH 7).

Dosing Regimen and Dosage: Using a method of the invention, AuNP solutions were intravenously administered to pigs via catheters in doses ranging from 1.88 mg-2 mg AuNP/kg of body weight. Serial blood (4-5 mL) draws from the catheter were performed at times ranging from 5 minutes to 24 hrs. For each time point, 2-5 animals injected with AuNPs were humanely sacrificed at times ranging from 30 minutes to 24 hours post injection. Various organs and tissues (heart, jejunum, brain, liver, spleen, kidneys, lungs, small intestine, and large intestine) were excised and weighed for analysis.

Figure 8:
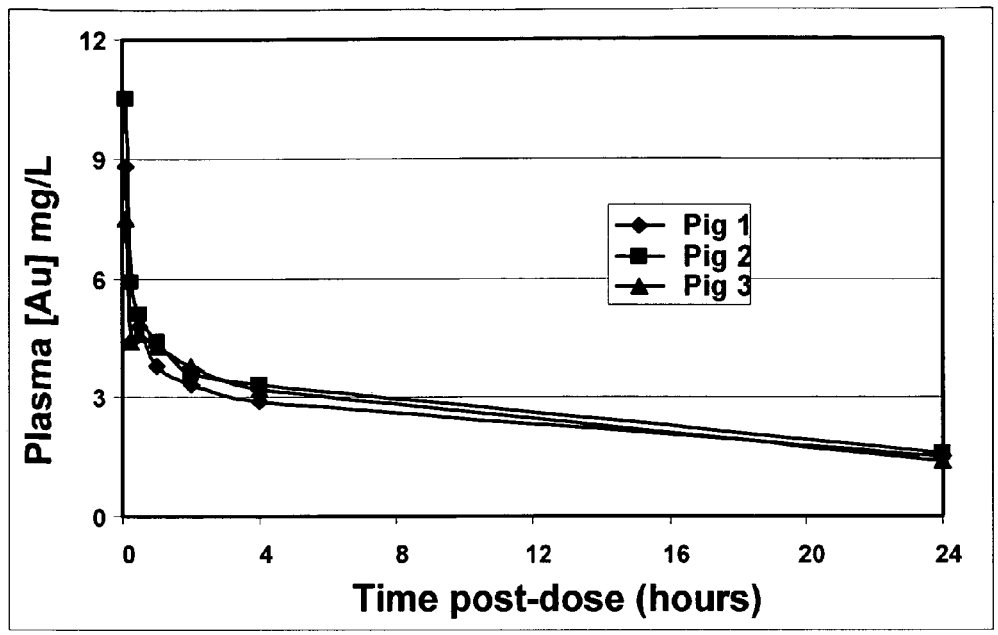
FIG. 8 illustrates the accumulation and clearance of GAAuNP's in one experiment.
Figure 9:
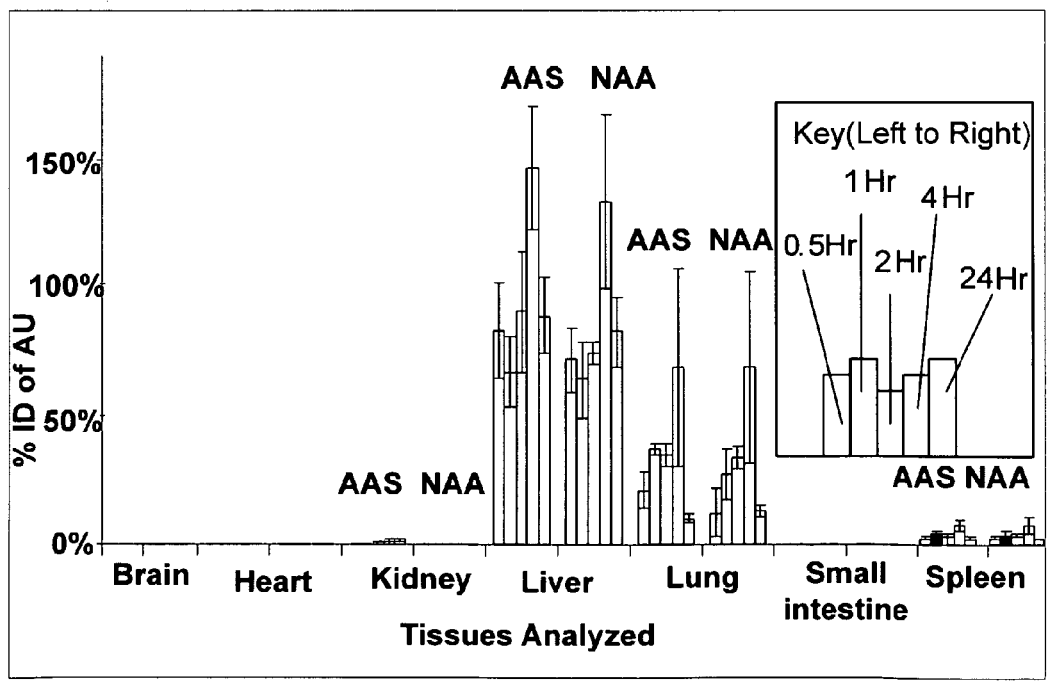
FIGS. 9-10 illustrate the uptake by various organs and tissues.
Figure 10:
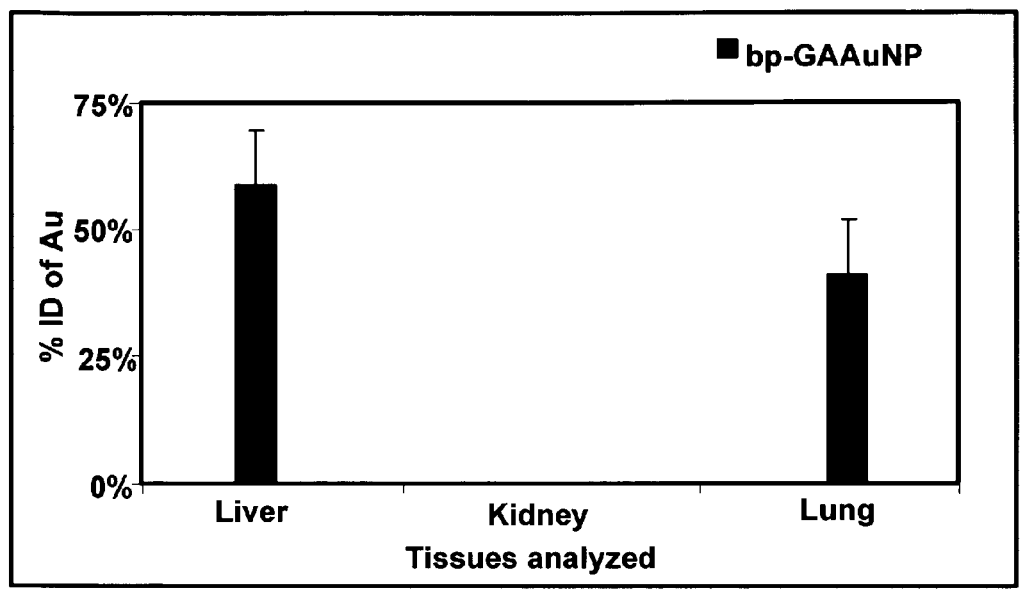

Results: The accumulation and clearance of GAAuNPs is shown in FIG. 8. The results in blood demonstrate facile clearance of metal nanoparticles from the blood stream. As shown by FIGS. 9-10, the uptake of GAAuNPs and bp-GAAuNPs is maximum in the liver, with lesser accumulation in lungs, and with much lower accumulation in other organs and tissue. FIG. 10 illustrates results at 24 hours.

Bio-Distribution Studies with AuNP-SS-BBN

Dosing Regimen and Dosage: Mice were dosed with 0.125 or 0.25 mL of the AuNP-SS-BBN (1 mg of gold conjugate in 1 mL of PBS) solutions via intraperitoneal route:

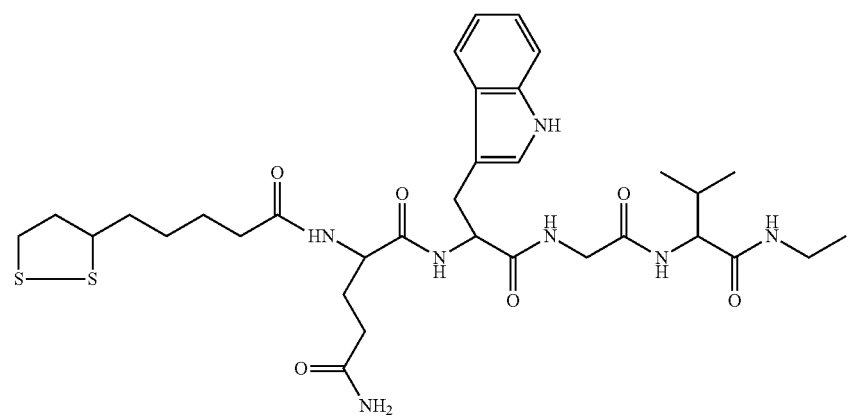

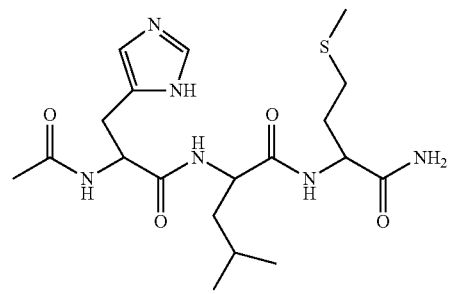

BBN (Bombesin) is a prostate and breast tumor specific peptide, and has been discovered to be particularly useful in invention embodiments as a functionalizing biomolecule. All mice were euthanized at 2 hours post dosing and blood, pancreas, liver, kidney, spleen, and lung were collected, weighed and frozen for NAA analysis.

Figure 11:
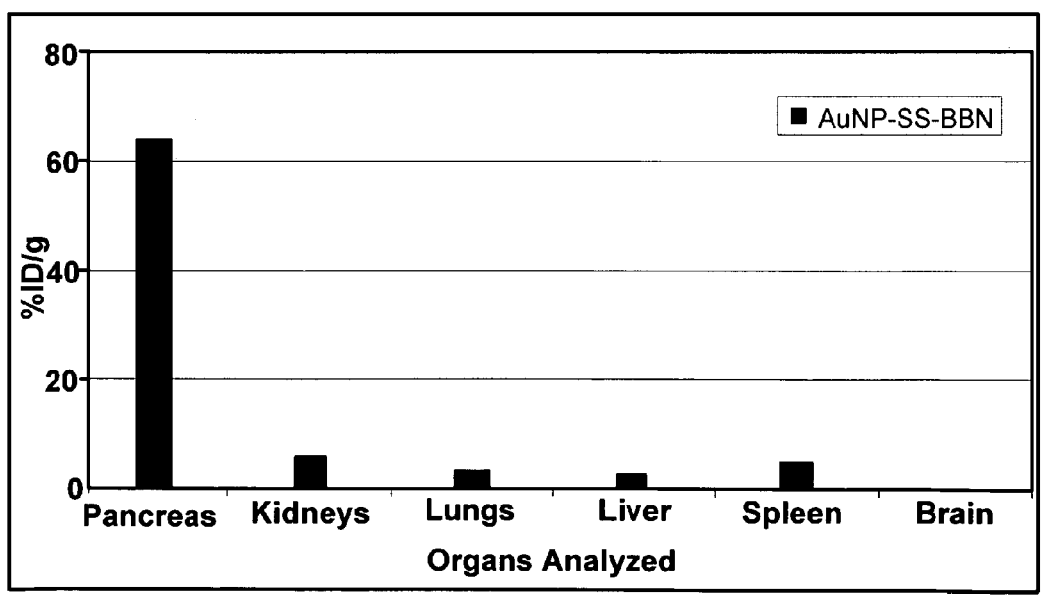
FIG. 11 illustrates the biodistribution of SAuNP-SS-BBN in mice at 2 hrs.

FIG. 11 illustrates the biodistribution of SAuNP-SS-BBN in the mice at 2 hrs of post-injection. As shown, the uptake of AuNP-SS-BBN was discovered to be maximum in the pancreas. Uptake is much lower in kidney, lung, liver and spleen. Uptake in the brain is still lower.

Sample Preparation: 1 g of tissue (±5%) was digested with 1 mL of trace metal concentrated nitric acid ($HNO^3$) in Teflon vials for 12 hours at 85° C. in an oven. Cooled samples were diluted to 10 mL with DI water. For NAA, the samples were prepared by placing approximately 100 mg of tissue (wet weight) into pre-cleaned high-density polyethylene irradiation vials. The weight of each sample was recorded and the irradiation vial was capped. Blanks, duplicates, and spiked samples were included in the AAS and NAA sample sets.

Atomic Absorption Spectroscopy (AAS): Brain, small intestine and heart were analyzed by furnace atomic absorption using a standard curve spanning 0-40 µg/L (corresponding to tissue gold levels of 0-0.4 µg/g). Furnace parameters were as specified in the User's Manual for the Perkin Elmer AAnalyst 800 ThGA graphite furnace. Detection level was 1 µg/L (0.01 µg/g). Quality control materials (duplicates, spikes and instrument calibration verification) were within appropriate ranges.

Liver, kidney, spleen and lungs were analyzed by flame atomic absorption using a standard curve of 0-4 mg/L (corresponding to tissue gold levels of 2-400 µg/g). Flame parameters were as specified in the Au method in the software for the Perkin-Elmer AAnalyst 800 flame methods. Duplicates and calibration verification materials were within appropriate ranges.

Neutron Activation Analysis (NAA): Samples were loaded in polyethylene transfer "rabbits" in sets of nine and were irradiated for 90 seconds in a thermal flux density of approximately $5 \times 10^{13}$ n $cm^{-2}$ $s^{-1}$. The samples were then allowed to decay for 24 to 48 hours and live time counted for 1200 seconds at a sample-to-detector distance of approximately 5 mm. The spectrometer consisted of a 21% high-purity germanium detector with a full-width-half-maximum resolution of 1.8 KeV at 1331 KeV, and a Canberra 9660 digital signal processor. Dead times ranged from 1% to 11%. The mass of Au was quantified by measuring the 411.8-keV gamma ray from the β-decay of 198Au ($t^{1/2}$=2.7 days). The area of this peak was determined automatically with the Genie ESP spectroscopy package from Canberra. Nine geometrically equivalent comparator standards were prepared by pipetting approximately 0.1 µg of Au from a 10.0±0.5 µg/mL certified standard solutions (high-purity standards) on paper pulp in the polyethylene irradiation vials. Analysis of the Au comparator standards yielded a relative specific activity (average and standard deviation) of 237239±6084 counts µg-1 Gd (n=9) with a relative standard deviation of 2.6%. The estimated concentration of AuNPs in different tissue was expressed in terms of percent injected dose (% ID) or % ID/g of tissue.

Additional Mouse Study

This study was undertaken to demonstrate the ability of gold nanoparticles (AuNP) of the invention and kits containing the same to provide x-ray image contrast in computed (CT) studies using a microCT scanner and mouse models. 8ICRSC-M-female mice were inoculated with 106 PC-3 cells on each bilateral flank. Tumors were allowed to grow for three weeks. At this time, the mice underwent whole-body CT scans at four time-points. 1) prior to injection with AuNP, 2) immediately following AuNP injection, 3) at twenty minutes following AuNP injection and 4) 72 hours following AuNP injection. Immediately following the fourth scan, animals were sacrificed, tissues were harvested, and the biodistribution of gold was determined using a neutron activation activity method. AuNP injections were directed into the tumor on the right flank of each mouse. Five mice received 30 µl of gum Arabic stabilized AuNP (CA-AuNP). Three others received an increased dose of between 40 and 60 µl. In all animals, CT images showed an increase in the attenuation due to the presence of AuNP and the tumor in the tumors. There was a conspicuous difference in the contrast between the tumor injected with AuNP and the tumor that was left as a control on the bilateral flank. The GA-AuNP was retained in the tumors at least 72 hours following the injection. The study further confirms that AuNP of the invention is useful for image contrast enhancement. The study also shows that GA-AuNP are retained within the tumors of the PC-3 xenograft model. Details of the study follow.

8 female ICRSC-M mice were inoculated with 106 PC3 (prostate cancer) cells/bilateral flank. The tumors were allowed to grow for 4 weeks. At the time of the imaging study, the tumors were approximately 200 to 300 mg in size.

Mice were scanned using the micro CT scanner at the Biomolecular Imaging Core at HST Veteran's Administration Hospital using the following protocol. 1) pre-dose CT scan immediately prior to injection, 2) injection of up to 60 µl of gum Arabic stabilized gold nanoparticles directly into one of the flank tumors, 3) a CT scan immediately following the injection, 4) a CT scan approximately 10 minutes following completion of the second CT scan, and 5) a CT scan conducted approximately 72 hours following the injection of GA-AuNP. GA-AuNP solutions contained 7 µg of Au per μl of solution. Following the completion of the last CT scan, the animals were sacrificed and organs and tumors were harvested and collected into vials for NAA analysis at MURR. This was to establish the actual concentration of gold nanoparticles in these tissues.

Images acquired with the microCT scanner using 80 kVp, 500 μA, 300 ms scans with 360 rotations. The cone-beam reconstruction provided image sets with 960×512×512 voxels with a voxel size of 103 μm³). In all eight animals, sufficient gold nanoparticle concentrations were present to demonstrate observable contrast change in the CT images. In all eight animals, the gold nanoparticles were retained within the tumor for at least 72 hours post-injection. Based on CT images, the gold nanoparticles tended to collect around the periphery of the tumor. In four of the animals, difficulty was encountered during the injection of gold nanoparticles because of the density of the tumor. Successful injection of the intended volume was achieved with 30 μl injections. In several of the animals, the attempt to inject up to 60 μl resulted in leakage from the tumor and an incomplete dose.

The mean CT number of the tumor increased in all eight cases, from an initial increase immediately following injection of the AuNP and then showing some decrease over time. In all cases, the gold nanoparticles tended to accumulate around the periphery of the tumor.

Results of NAA show that the right flank tumors retained most of the gold. In one case (Mouse B), the nanoparticles may have entered the vascular system and distributed to the liver and the kidneys, as has been observed for these nanoparticles in the swine model. Gold nanoparticles were retained in the tumor injected and did not cross over to the left flank tumor.

This study demonstrates that gold nanoparticles of the invention produce image contrast in CT scans of a small animal model. The intratumoral injection may be useful in some applications, but also may not prove to be the optimal route in all clinical applications. Intratumoral injection was mostly successful in the retention of nanoparticles in the tumor with some exception. We speculate that during the injection of animals B and F, nanoparticles were injected into vasculature, resulting in higher uptake of the nanoparticles in other organs (live and spleen). Even with this lower retention, there was still enough concentration to visualize contrast. This emphasizes the importance of targeted nanoparticles (which this effort did not involve).

What is claimed is:

1. A kit for providing a contrast enhancer in a mammal for contrasting during imaging of the mammal, the kit consisting of:
   gold nanoparticles functionalized with a biomolecule for engagement with a target portion of the mammal, wherein the gold nanoparticles are directly coated with bisphosphonate and gum arabic; and
   an aqueous solution of the gum arabic.

2. A kit as defined by claim 1 wherein the coated gold nanoparticles are functionalized with a bombesin molecule, and wherein the target portion of the mammal comprises a lesion.

3. A kit as defined by claim 1 wherein the coated gold nanoparticles are provided in a dosage sufficient to cause engagement between a target portion of the mammal in a ratio of at least 1 mg gold nanoparticles/gm of target portion of the mammal.

4. A kit as defined by claim 1 wherein the coated gold nanoparticles are configured to allow a period of at least about 24 hours after injection into the mammal before using an imaging apparatus to perform imaging on the mammal.

5. A kit as defined by claim 1 wherein the coated gold nanoparticles have a diameter of less than about 20 nm and the target portion of the mammal is the lungs.

6. A kit as defined by claim 1 wherein the coated gold nanoparticles have a diameter of greater than about 20 nm and the target portion of the mammal is one or more of the liver and the spleen.

7. A kit as defined by claim 1 wherein the coated gold nanoparticles are provided in a dosage of between about 2 and about 45 mg per kilogram body weight of the mammal.

8. A kit as defined by claim 1 wherein the coated gold nanoparticles are provided in a dosage of between about 1 and about 5 mg per kilogram body weight of the mammal.

9. A kit as defined by claim 1 wherein the target portion of the mammal comprises one or more of an organ, tissue or a lesion.

* * * * *